United States Patent [19]

Grasso

[11] Patent Number: 4,955,378
[45] Date of Patent: Sep. 11, 1990

[54] APPARATUS AND METHODS FOR PERFORMING ELECTROFUSION AT SPECIFIC ANATOMICAL SITES

[75] Inventor: Robert J. Grasso, Tampa, Fla.

[73] Assignee: University of South Florida, Tampa, Fla.

[21] Appl. No.: 297,218

[22] Filed: Jan. 17, 1989

Related U.S. Application Data

[63] Continuation-in-part of Ser. No. 189,206, May 2, 1988.

[51] Int. Cl.$^5$ .............................................. A61N 1/32
[52] U.S. Cl. .................................... 128/421; 128/788; 128/793; 604/20; 435/172.2; 435/173; 935/89
[58] Field of Search .................. 128/419 R, 421, 783, 128/784, 793, 802, 803, 788; 604/20; 435/172.2, 173; 935/89

[56] References Cited

U.S. PATENT DOCUMENTS

| | | | |
|---|---|---|---|
| 2,525,381 | 10/1950 | Tower | 128/793 X |
| 3,122,137 | 2/1964 | Erlanger | 128/793 X |
| 3,669,119 | 6/1972 | Symmes | 128/793 |
| 4,016,886 | 4/1977 | Doss et al. | 128/804 |
| 4,121,592 | 10/1978 | Whalley | 128/804 X |
| 4,141,359 | 2/1979 | Jacobsen et al. | |
| 4,326,529 | 4/1982 | Doss et al. | 128/303.1 |

FOREIGN PATENT DOCUMENTS 2351670  9/1975  France ................................. 604/20

OTHER PUBLICATIONS

Heller et al., Abstract B-188, Abstracts of the Annual Meeting-1988, p. 61.
Heller et al., Abstract 128, FASEB Journal, 2(4), 1988.

*Primary Examiner*—Lee S. Cohen
*Attorney, Agent, or Firm*—Joseph C. Mason, Jr.; Ronald E. Smith

[57] ABSTRACT

Electrofusion of biological particles to specific areas of tissue is accomplished in vivo through the use of electrode members that conform to the configuration and dimension of the tissue at the electrofusion site. The electrode members are positioned in close physical proximity to one another so that when an electrical potential difference is established between them, current flow is limited to the area of tissue between the electrodes so that tissue remote from the selected electrofusion site is substantially unaffected by such current flow. A general apparatus and method is supplemented with two illustrative apparatus and methods for accomplishing in vivo electrofusion on corneas and in cervical areas.

11 Claims, 2 Drawing Sheets

APPARATUS AND METHODS FOR PERFORMING ELECTROFUSION AT SPECIFIC ANATOMICAL SITES

CROSS-REFERENCE TO RELATED APPLICATIONS

The present application is a continuation-in-part of a co-pending application filed by the present inventor on May 2, 1988, entitled "Method for Electrofusing Biological Particles to Tissues," Ser. No. 07/189/206.

TECHNICAL FIELD

This invention relates, generally, to devices and methods having utility in connection with cell-tissue electrofusion accomplished in vitro, in situ, or in vivo. More particularly, it relates to electrode members and related apparatus that confine an induced DC field to a specific animal or human anatomical area.

BACKGROUND ART

The above-referenced disclosure filed May 2, 1988 contains a thorough discussion of the prior art pertinent to the present invention and such disclosure is incorporated herein by reference and made a part hereof.

In the earlier disclosure, it was mentioned that biological particles to be fused onto tissue in the host animal or plant are deposited on a support means and brought into physical contact with tissue at the preselected electrofusion site. Mechanical pressure is applied to the support means to bring the particles and tissue into still closer physical contact and a DC pulse generator is activated to achieve the desired electrofusion.

A second or ground electrode was positioned in electrical communication with a second preselected anatomical area, and one or more DC pulses were passed from the first electrode to ground through the anatomical tissue between said first and second preselected anatomical areas.

Accordingly, the disclosed apparatus included no specific means for confining the path of electrical current as it flowed through the body of the host from the first electrode to the second. Since electrical current follows the path of least resistance, a pulse applied to the first electrode could travel along many differing paths throughout the animal or human's body before arriving at the ground electrode. Thus, the earlier apparatus was restricted to low current applications.

There is a need for an improved cell-tissue, tissue-tissue and liposome-tissue fusion apparatus that restricts current flow to the inter-electrode space only, but the prior art contains no teachings or suggestions concerning how the art could be advanced.

DISCLOSURE OF INVENTION

The present invention is illustrated in three exemplary embodiments which suggests numerous derivative embodiments.

All of the embodiments will be referred to as having utility in connection with cell-tissue electrofusion, but it should be understood that the present invention has equal utility in connection with tissue-tissue electrofusion and liposome-tissue electrofusion as well. Moreover, it should be understood that this invention has utility in in vivo in vitro and in situ applications.

The first embodiment has general application and is suitable for use at virtually any cell-tissue electrofusion site. It consists of a pair of electrode members, each of which is electrically coupled to a DC pulse generator, that are disposed on opposite sides of an electrofusion site. The oppositely polarized electrodes are positioned in as close proximity to each other as is practicable to insure that the electrofusing current will follow a direct path of travel between the electrodes. In this manner, the possibility that current might stray and inflict trauma at anatomical sites remote from the electrofusion site is minimized.

The electrodes of the second and third embodiments of the present invention are site-specific electrodes in that they relate to electrofusion processes that are performed on the eye of an animal or human and the cervical area of an animal or human, respectively.

More specifically, both of the electrodes of the second embodiment are housed in an insulated monolithic housing adapted to properly position the electrodes with respect to an animal or human eye. An electrode of a first polarity is specifically configured and dimensioned to conform to the contour of the cornea of an eye so that it may overlie the same and be pressed tightly thereagainst without inflicting trauma. An electrode of a second polarity has an annular configuration so that it overlies and encircles the anterior sclera portion of the eye. Accordingly, activation of a DC pulse generator to which the electrodes are electrically coupled produces a current flow which flows in a generally radial pattern from the first electrode at the electrofusion site to the second, ring-shaped electrode which circumscribes the anterior sclera portion of the eye. Thus, the chance that current might stray to the optic nerve and hence to the brain is minimized.

The third embodiment includes a pair of oppositely polarized electrodes that are introduced into the cervical area. A first electrode has hinged portions that are outwardly deployable once inserted into the uterus to abuttingly engage the uterine side of the cervix; a second electrode abuttingly engages the vaginal side of the cervix. Thus, the cervical area is sandwiched between the electrodes so that when a DC pulse generator is activated, currents are substantially confined to the area between the electrodes.

The apparatus of the third embodiment further includes a light source and an insulated housing member for the leads that couple the electrodes to the pulse generator.

It is therefore understood that an important object of the present invention is to advance the art of cell-tissue, tissue-tissue, liposome-tissue electrofusion by providing electrodes that confine the electrofusion current to the precise site of electrofusion and to immediately adjacent tissue.

More specific objects include the provision of electrodes particularly adapted to accomplish cell-tissue, tissue-tissue, liposome-tissue electrofusion in ocular and cervical regions while minimizing the probabilities of stray currents inflicting trauma on anatomical areas of the body contiguous to such sites or remote therefrom.

The invention accordingly comprises the features of construction, combination of elements and arrangement of parts that will be exemplified in the descriptions set forth hereinafter and the scope of the invention will be set forth in the claims.

BRIEF DESCRIPTION OF DRAWINGS

For a fuller understanding of the nature and objects of the invention, reference should be made to the following detailed description, taken in connection with the accompanying drawings, in which.

BEST MODES FOR CARRYING OUT THE INVENTION

Figure 1:
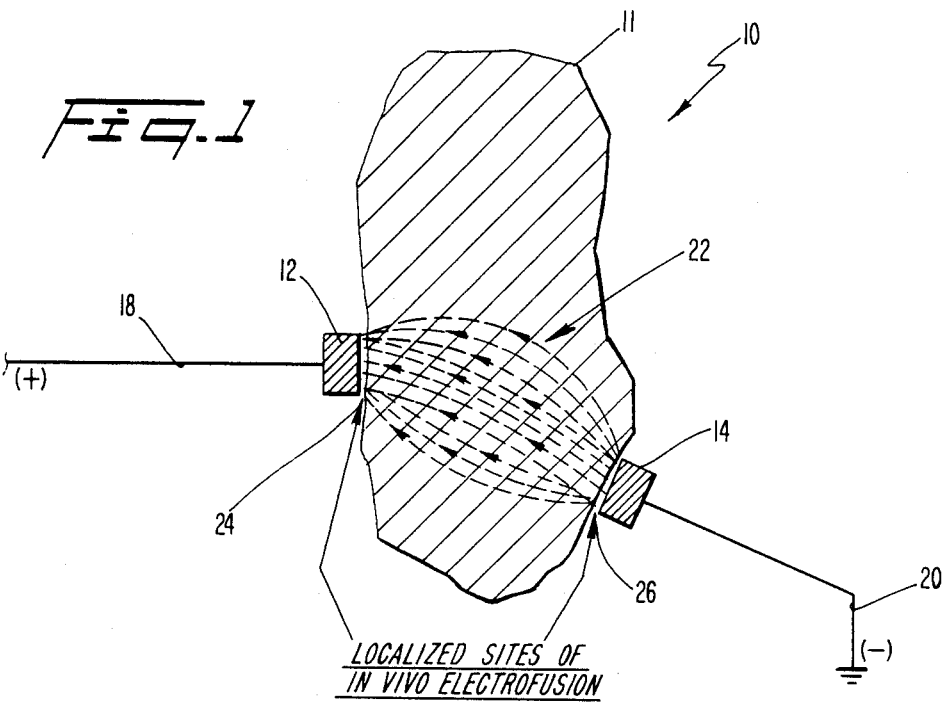
FIG. 1 is a diagrammatic view showing how the electrodes of the first embodiment of this invention are positioned with respect to preselected tissue.

Referring now to FIG. 1, it will there be seen that a novel apparatus having utility in connection with cell-tissue electrofusion is designated by the reference numeral 10 as a whole.

Again, although apparatus 10 and the other apparatus to be disclosed in detail hereinafter will be identified as having utility in connection with cell-tissue electrofusion, it should be understood from the outset that such reference is made for purposes of brevity only since all embodiments of the present invention also have utility in connection with tissue-tissue electrofusion and liposome-tissue electrofusion.

In FIG. 1, a preselected tissue 11 is shown disposed in sandwiched relation between a first or positive electrode 12 and a second or ground electrode 14. Lead 18 electrically couples electrode 12 to the positive side of a DC pulse generator (not shown) and lead 20 electrically couples electrode 14 to a suitable ground.

Since tissue 11 offers a path of low electrical resistance, activation of the pulse generator results in an electrical current between electrodes 12 and 14. The current flow induces an electrical field denoted 22 in FIG. 1.

Advantageously, field 22 is localized or confined, i.e., it is restricted to the region between the electrodes.

Electrofusion of biological particles to the tissue occurs when the respective electrodes 12, 14 overlie tissue 11; more specifically, electrofusion sites associated with electrodes 12 and 14 are denoted 24 and 26, respectively. For a fuller understanding of how the electrofusion takes place, reference should be made to the cross-referenced disclosure. Generally, electrofusion is preferably accomplished under constant voltage conditions by applying to the electrode three square wave twenty microsecond pulses of direct current with an amplitude of twenty volts at a pulse rate of one pulse per second.

The apparatus of FIG. 1 has particular utility in connection with in vivo electrofusion procedures, but it can be employed in in vitro and in situ applications as well.

Its particular utility in connection with in vivo applications arises because particular care must be taken in in vivo applications where animals or humans are involved to insure that electrical currents do not flow through areas of the anatomy that might suffer trauma as a result of such current flow. For example, if tissue 11 were positioned near the heart of the animal or human, it would be of the utmost importance to confine the current flow to the anatomical region between the electrodes.

Figure 2:
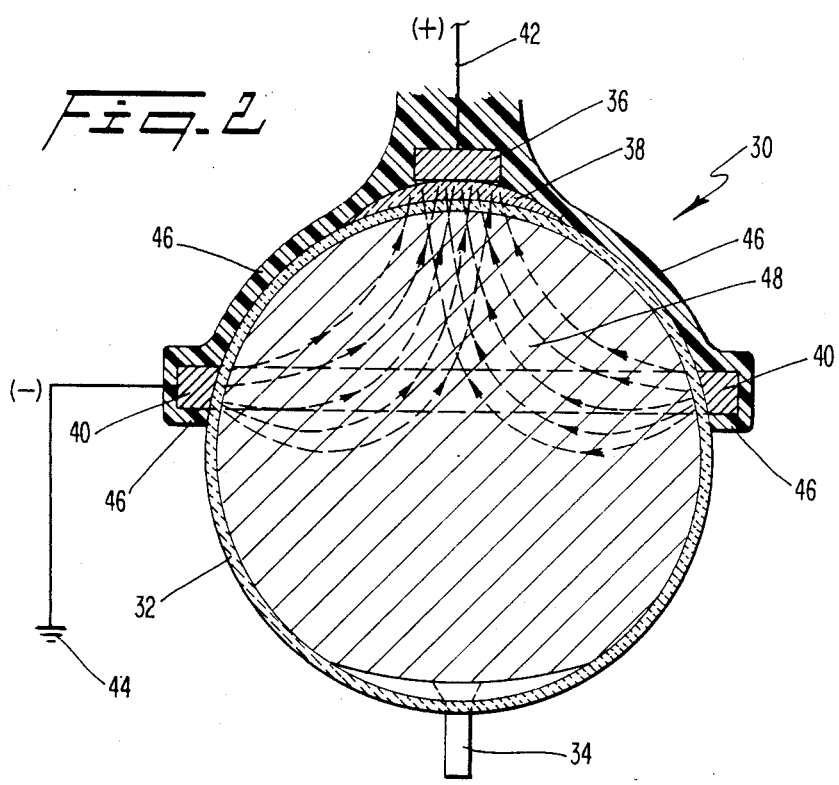
FIG. 2 is a diagramatic view showing how the electrodes of the second embodiment of this invention are positioned with respect to a human or animal eye, said electrodes and eye being shown in cross-section.
Figure 3:
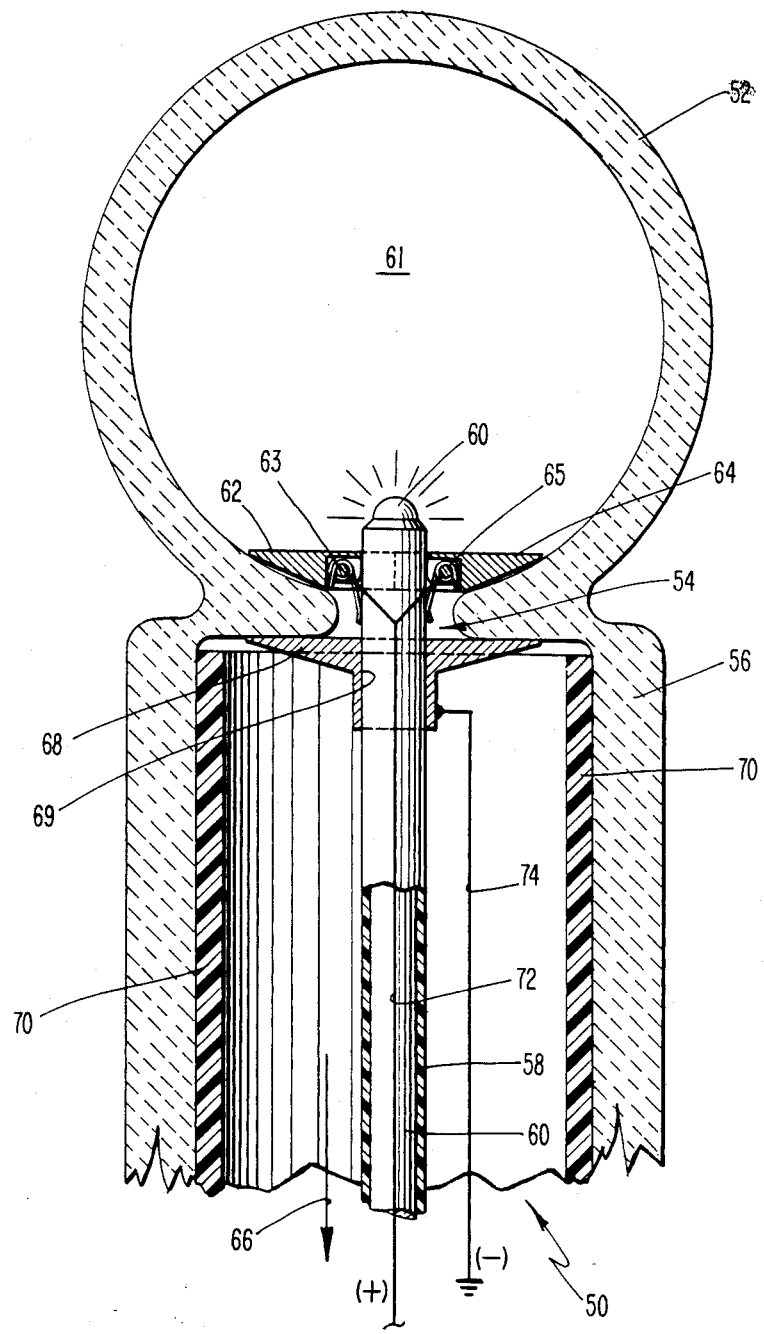
FIG. 3 is a diagramatic view showing how the electrodes of the third embodiment are positioned with respect to the cervical area of an animal or human.

The second and third embodiments of this invention, shown in FIGS. 2 and 3, respectively, further illustrate this important teaching of this invention.

The environment of the second embodiment is denoted 30 as a whole in FIG. 2. An animal or human eye 32 is depicted in section; optic nerve 34 connects the eye to the brain (not shown). In an in vivo situation, it is of paramount importance to insure that no stray electrical currents find their way to the optic nerve 34 and hence to the brain.

The novel apparatus that insures against electrical current flow to the brain includes a first electrode 36 that is specifically configured and dimensioned to overlie the cornea 38, i.e., the cornea-contacting side of electrode 36 conforms to the shape of the cornea, and a second annular in configuration electrode 40.

For reasons disclosed in detail in the cross-referenced disclosure, electrode 36 conforms to the size and shape of the cornea so that said electrode can be tightly pressed against the cornea without inflicting trauma to the eye. The tight abutting engagement between electrode 36 and cornea 38 facilitates the electrofusion process and enhances the performance of the electrical-field confining apparatus as well.

Ring-shaped electrode 40 is positioned on the anterior sclera portion of the eye in circumscribing relation thereto as shown.

The cornea-overlying electrode 36 is electrically coupled to a DC pulse generator by lead 42 and ring electrode 40 is grounded as at 44 (or vice versa).

Both electrodes 36, 40 are mounted in an insulated housing means, generally denoted 46; housing means 46 maintains the electrodes in their operative configuration and of course electrically insulates them from one another.

Current generated by the pulse generator thus flows between electrodes 36 and 40 when the generator is activated, and such current induces an electrical field denoted 48 in FIG. 2. It should be understood that the current flow is generally radial in that ring electrode 40 is conductive along its entire circumferential extent.

It is clear from FIG. 2 that stray currents are suppressed, i.e., the current is effectively confined to the inter-electrode space. The current flow, represented by field lines 48 as aforesaid, is thus remote from optic nerve 34 as desired, and an important object of this invention is achieved.

Electrofusion occurs at the cornea 38/electrode 36 interface.

In the cross-referenced disclosure, a cornea-contacting electrode such as electrode 36 was generally disclosed; it was placed onto the cornea 38 of a live rabbit. However, in such disclosure there was no teaching or suggestion of ring electrode 40. Instead, the ground electrode was attached to the rabbit's buccal mucosa, i.e., to the inside of the rabbit's cheek. As such, current was allowed to flow between the cornea and the cheek. Although no rabbit experienced any trauma from these pioneering electrofusion experiments, the possibility that electrical current could stray to the animal's brain via the optic nerve existed. This possibility provided the impetus for the present inventions.

The apparatus of FIG. 2 could be used to accomplish electrofusion on parts of the anatomy other than an eye. Indeed, in view of the present teachings and suggestions, the number of different site-specific electrofusion apparatuses that could be constructed is limited only by the imagination of the machine designer and such designs are also within the scope of these Letters Patent.

For example, an electrofusion device specifically designed for use in in vivo applications in the cervical area is denoted as a whole by the reference numeral 50 in FIG. 3.

In FIG. 3, the uterine wall is denoted 52, the cervix is denoted 54, and the vaginal wall is denoted 56.

Electrofusion device 50 includes a hollow uterine probe member 58 within which is positioned an optical fiber 60 to illuminate the uterine area or cavity 61 as suggested by the truncate radial lines in the vicinity of fiber 60.

A pair of hingedly mounted electrode members 62, 64 are rotatably mounted about hinge posts 63, 65, respectively, near the distal free end of probe member 58 as shown; the position of electrodes 62, 64 is under the control of a mechanical means (not shown) at the proximal end of probe 58 as suggested by the directional arrow 66.

When properly positioned in the manner hereinafter described, electrodes 62, 64 will overlie the uterine cervical area as shown.

A centrally apertured, generally disc-shaped electrode 68, when properly positioned, will overlie the vaginal cervical area as shown. It is placed into its illustrated position by aligning its central aperture 69 with probe 58 and sliding it in a proximal-to-distal direction. Clearance space for insertion of disc-shaped electrode 68 is provided by cylindrical insulator member or dilator 70.

In vivo installation of the novel apparatus is accomplished under general anesthesia by insertion of the insulated dilator member 70, the outer cylindrical walls of which are suitably lubricated, until the distal end of the dilator abuts the peripheral cervical epithelium, insertion of probe member 58, with the aid of illumination provided by optical fiber 60, through the cervix 54 with the hinged electrodes 62, 64 in their folded configuration, deployment of the hinged electrodes 62, 64 into their FIG. 3 configuration through manipulation of the mechanical control means, and insertion of disc-shaped electrode 68 until the cervical area is held in sandwiched relation between the respective electrodes as shown.

Electrical lead 72 electrically couples hinged electrodes 62, 64 to a DC pulse generator, not shown, and lead 74 electrically couples disc electrode 68 to ground, or vice versa. In vivo electrofusion takes place where the respective electrodes abut cervical tissue and electrical currents (not shown to simplify the drawing) are confined to the small area between the electrodes.

Thus, all three of these specifically disclosed embodiments of this invention employ a pair of closely spaced electrodes of opposite electrical polarity so that electrical currents are confined to a localized area between such electrodes.

INDUSTRIAL APPLICABILITY

This invention has many biological, biomedical, clinical and veterinary applications. Use of the novel electrodes in the electrofusion of selected biological particles to histiologically intact tissue facilitates the electrofusion process itself while protecting the animal or human patient against stray electrical currents. Thus, the novel electrodes advance the arts of cell-tissue electrofusion, liposome-tissue electrofusion and tissue-tissue electrofusion.

The utility of electrofusion in creating bioengineered animal models is disclosed in the cross-referenced disclosure, although such disclosure could not be exhaustive in view of the wide range of possible applications of the electrofusion process.

As an example of the broad range of applications for the present invention not already disclosed in the earlier disclosure, it is contemplated that electrofusion in general and electrofusion employing current-localizing electrodes of the type disclosed herein could be employed in helping patients recover from operations.

For example, cartilage is removed from knee joints during bone spur removal operations. The electrofusion of the patient's own chondrocytes, collected from adjacent anatomical locations, to the denuded area would certainly accelerate the formation of new cartilage in the absence of immunological rejection.

This is just one example of the plurality of applications of this invention. In view of the breakthrough nature of the technology herein disclosed, the claims appended hereto are entitled to a broad construction, as a matter of law, so as to protect the heart of this pioneering invention.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A device for confining flow of electrons through living tissue to a preselected area of said tissue, comprising:
   a first electrode means adapted to be disposed in abutting relation to a first preselected area of tissue;
   a second electrode means, generally annular in configuration, adapted to be disposed in abutting relation to a second preselected area of tissue having a generally spherical shape, said second preselected area of tissue being in closely spaced proximity to said first preselected area of tissue;
   a source of electrical power;
   means for electrically coupling said source of electrical power to said first electrode means; and
   means for grounding said second electrode means;
   whereby in vivo electrofusion occurs at the interface of said first preselected area of tissue and said first electrode means.

2. The device of claim 1, wherein said source of electrical power is a pulse generator.

3. The device of claim 2, wherein said source of electrical power is a DC pulse generator.

4. The device of claim 3, wherein said first electrode means is configured and dimensioned to conform to the contour of said first preselected area of tissue.

5. The device of claim 4, wherein said first preselected area of tissue is the cornea of an eye and wherein said first electrode means is specifically configured and dimensioned to conform to the contour of said cornea.

6. The device of claim 5, wherein said second electrode means is specifically configured to conform to the contour of the sclera portion of an eye.

7. The device of claim 6, further comprising an insulated housing means that houses said first and second electrode means in a predetermined fixed spatial relationship to one another.

8. A method of passing electrical current through preselected living tissue to accomplish in vivo electrofusion, comprising the steps of:
   depositing biological particles upon a first electrode means;
   positioning said first electrode means and said biological particles deposited thereupon in abutting relation to a first preselected area of tissue;
   configuring and dimensioning a tissue-contacting side of said first electrode means to conform to the contour of said tissue at said first preselected area;
   positioning a second electrode means in abutting relation to a second preselected area of tissue;
   configuring and dimensioning a tissue-contacting side of said second electrode means to conform to the contour of said tissue at said second preselected area; and
   imposing a preselected electrical potential difference between said first and second electrode means to accomplish said electrofusion.

9. The method of claim 8, further comprising the step of spacing said first and second electrode means in close physical proximity to one another so that electrical current through areas of tissue remote from said preselected areas of tissue is limited.

10. A method of accomplishing in vivo electrofusion of biological particles to an anatomical part of generally spherical configuration, comprising the steps of:
    depositing preselected biological particles upon a first electrode means;
    configuring and dimensioning said first electrode means to conform to the contour of a substantially central portion of said generally spherical anatomical part;
    positioning said first electrode means and said biological deposited thereupon in abutting, overlying relation to said substantially central portion of said generally spherical anatomical part;
    forming a second electrode means into a generally annular configuration;
    positioning said second electrode means into abutting relation to said anatomical part and in circumscribing relation to said first electrode means; and
    establishing an electrical potential difference between said first and second electrode means to thereby accomplish in vivo electrofusion of said biological particles to said anatomical part.

11. A method of accomplishing in vivo electrofusion of biological particles to the cornea of an eye, comprising the steps of:
    configuring and dimensioning a first electrode means to conform to the contour of a cornea;
    depositing biological particles upon said first electrode means;
    positioning said first electrode means and biological particles deposited thereupon into overlying relation to said cornea;
    configuring and dimensioning a second electrode means into a generally annular form, specifically into a form that conforms to the sclera portion of the eye;
    positioning said second electrode means into abutting, overlying relation to the sclera portion of said eye; and
    establishing an electrical potential difference between said first and second electrode means to thereby accomplish in vivo electrofusion of said biological particles to the cornea of an eye.

* * * * *